(12) United States Patent
Johansson et al.

(10) Patent No.: US 9,074,018 B2
(45) Date of Patent: Jul. 7, 2015

(54) RECONSTITUTED PULMONARY SURFACTANTS

(71) Applicant: CHIESI FARMACEUTICI S.p.A, Parma (IT)

(72) Inventors: Jan Johansson, Parma (IT); Tore Curstedt, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 14/085,125

(22) Filed: Nov. 20, 2013

(65) Prior Publication Data

US 2014/0142021 A1    May 22, 2014

(30) Foreign Application Priority Data

Nov. 21, 2012 (EP) .................... 12193708

(51) Int. Cl.
*A61K 38/00* (2006.01)
*C07K 14/785* (2006.01)

(52) U.S. Cl.
CPC ............... *C07K 14/785* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,053,044 B1 | 5/2006 | Curstedt et al. | |
| 7,511,011 B2 | 3/2009 | Curstedt et al. | |
| 7,638,493 B2 * | 12/2009 | Lee et al. | 514/1.1 |
| 7,842,664 B2 | 11/2010 | Curstedt et al. | |
| 8,148,492 B2 | 4/2012 | Johansson et al. | |
| 8,183,210 B2 | 5/2012 | Johansson et al. | |
| 8,399,406 B2 | 3/2013 | Pivetti et al. | |
| 2010/0004173 A1 * | 1/2010 | Johansson et al. | 514/12 |
| 2013/0079275 A1 | 3/2013 | Johansson et al. | |

FOREIGN PATENT DOCUMENTS

| | | |
|---|---|---|
| WO | 00/47623 | 8/2000 |
| WO | 2008/044109 | 4/2008 |

OTHER PUBLICATIONS

European Search Report in Application No. 12193708.0 issued Apr. 15, 2013.
Nicola Pelizzi et al., "Rapid Communications in Mass Spectrometry", vol. 16, No. 24 (2002) pp. 2215-2220.
Blanco et al., "Biotechnologia Aplicada", vol. 29, No. 2 (2012) pp. 53-59.
Curosurf Poractant alfa (Phospholipid fraction of porcine lung) 80 mg/ml (2012) 8 pages.

* cited by examiner

*Primary Examiner* — Karlheinz R Skowronek
*Assistant Examiner* — Roy Teller
(74) *Attorney, Agent, or Firm* — Oblon, McClelland, Maier & Neustadt, L.L.P.

(57) ABSTRACT

The present invention is directed to a reconstituted surfactant comprising a phospholipid mixture, and a combination of particular analogues of the native surfactant protein SP-C with analogues of the native surfactant protein SP-B. The invention is also directed to pharmaceutical compositions and kits thereof and to its use for the treatment or prophylaxis of RDS and other respiratory disorders.

19 Claims, 10 Drawing Sheets

RECONSTITUTED PULMONARY SURFACTANTS

CROSS REFERENCES TO RELATED APPLICATIONS

This application claims priority to European Patent Application No. 12193708.0, filed on Nov. 21, 2012, which is incorporated herein by reference in its entirety.

BACKGROUND OF THE INVENTION

1. Field of the Invention

The present invention relates to synthetic pulmonary surfactants for the treatment or prophylaxis of respiratory distress syndrome (RDS) in premature infants and other respiratory disorders. In particular, present the invention relates to a reconstituted surfactant comprising a combination of particular analogues of the native surfactant protein SP-C with analogues of the native surfactant protein SP-B and a phospholipid mixture.

2. Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is composed primarily of lipid and contains minor amounts of various proteins. An absence of adequate levels of this complex results in malfunction of the lung. This syndrome is called Respiratory Distress Syndrome (RDS) and it commonly affects preterm infants.

Said syndrome is effectively treated with modified natural surfactant preparations extracted from animal lungs. Commercially available modified surfactant preparations are, for example, poractant alfa (Curosurf™), derived from porcine lung, calfactant (Infasurf™), extracted form calf lung lavage, and beractant (Survanta™), a chemically modified natural bovine lung extract.

The main constituents of these surfactant preparations are phospholipids, such as 1,2-dipalmitoyl-sn-glycero-3-phosphocholine (DPPC), (PG), and surfactant hydrophobic proteins B and C(SP-B and SP-C).

Due to the drawbacks of the surfactant preparations from animal tissues, such as the complication of the production and sterilization processes and possible induction of immune reactions, synthetic surfactants seeking to mime the composition of the modified natural surfactants have been developed. However, according to the available literature, none of the synthetic surfactants developed so far has shown the same efficacy as that of the surfactants extracted from animals.

A possible explanation is that the available reconstituted surfactants developed so far do not reproduce the complete proteinaceous profile of the modified natural surfactants as the former comprise only one proteinaceous (peptide) component.

For these reasons, reconstituted surfactants comprising both analogues of the native surfactant proteins SP-B and SP-C have been proposed in the art, for instance in WO 2008/044109, WO 2008/011559, and WO 2010/139442, all of which are incorporated herein by reference in their entireties.

In WO 2004/105726, which is incorporated herein by reference in its entirety, the use of lipid mixture comprising polyunsaturated phospholipids with the aim of reducing the viscosity of synthetic surfactants has been disclosed.

In spite of that, there is still skepticism regarding the possibility that reconstituted surfactants could achieve the same efficacy in terms of lung compliance of that of the surfactants extracted from animals, in particular in terms of lung gas volumes and grade of alveolar patency at the end of expiration.

So it would be highly advantageous to provide reconstituted surfactants comprising phospholipid mixtures capable of improving the properties in terms of lung compliance.

Thus, there remains a need for reconstituted surfactants with improved properties.

SUMMARY OF THE INVENTION

Accordingly, it is one object of the present invention to provide novel reconstituted surfactants.

It is another object of the present invention to provide novel reconstituted surfactants which afford improved lung compliance.

It is another object of the present invention to provide novel methods of treating respiratory distress syndrome by administering such a reconstituted surfactant.

These and other objects, which will become apparent during the following detailed description, have been achieved by the inventors' discovery of a reconstituted surfactant comprising a lipid carrier, and a combination of a particular polypeptide analogue of the native surfactant protein SP-C with a particular polypeptide analogue of the native surfactant protein SP-B.

In particular the present invention provides a reconstituted surfactant comprising:

a phospholipid mixture;

a polypeptide analogue of the native surfactant protein SP-B; and a polypeptide analogue of the native surfactant protein SP-C represented by the general formula:

(SEQ ID NO: 1)
IPSSPVHLKRLKLLLLLLLLILLLILGALLΩ$_p$G$_p$L$_p$ (I)

in which:

Ω is an amino acid selected from the group consisting of M or M oxidized on the sulfur atom, I, L, and nL;

p is 0 or 1 said phospholipid mixture consisting of:

i) an amount of about 50% by weight of DPPC;

ii) an amount of about 10% by weight of POPG; and iii) an amount of about 40% by weight of a naturally-derived fraction of unsaturated phospholipids consisting essentially of:

from 30 to 50% of POPC, from 10 to 20% of PLPC, from 4 to 10% of P(:1)OPC, from 5 to 8% of SLPC, from 5 to 8% of OPC, from 1 to 3% of SAPC, from 5 to 15% of SOPC, from 1 to 2% of PAPC, from 1 to 3% of PDPC, from 0 to 3.5% of SOPE, from 0 to 8% of SAPE, from 0 to 4% of SLPE, from 0 to 2.5% of PLPE, from 0 to 3.5% of POPE; from 0 to 2.0% of LAPE, from 0 to 2.% of LLPE, and from 0 to 10% of PSM; all the amounts i), ii) and iii) being calculated based on the total weight of the phospholipid mixture.

The present invention also provides pharmaceutical compositions comprising the claimed reconstituted surfactant alone or in combination with one or more pharmaceutically acceptable carriers.

The present invention also provides the use of the claimed reconstituted surfactant as a medicament.

In a further aspect, the present invention provides the use of the claimed reconstituted surfactant for the prophylaxis and/or treatment of respiratory distress syndrome (RDS) and other respiratory disorders.

Moreover, the present invention provides the use of the claimed reconstituted surfactant for the manufacture of a medicament for the prophylaxis and/or treatment of respiratory distress syndrome (RDS) and other respiratory disorders.

The present invention also provides a method for the prophylaxis and/or treatment of respiratory distress syndrome (RDS) and other respiratory disorders, said method comprising administering to a patient in need of such treatment a therapeutically effective amount of the reconstituted surfactant mentioned above.

The present invention is also directed to a kit, comprising: a) the reconstituted surfactant of the invention in a powder form in a first unit dosage form; b) a pharmaceutically acceptable carrier in a second unit dosage form; and c) container means for containing said first and second dosage forms.

In this respect, the applicant has found that, in addition to the proteinaceous profile, the phospholipid composition is also very important to stabilize the alveoli at the end of expiration.

In particular, the applicant found that reconstituted surfactants comprising representative analogues of the proteins B and C disclosed in WO 2008/044109 and the phospholipid fraction extracted from poractant alfa, which is rich of unsaturated phospholipids, give results which overlap those of poractant alfa regarding tidal volumes and lung gas volumes.

Thus, it has now been found, and it is the object of the present invention, that naturally-derived fraction enriched in unsaturated phospholipids can be advantageously combined with particular analogues of the native SP-C protein, and with particular analogues of the native protein SP-B in order to provide reconstituted surfactants preparation with properties, in terms of tidal volumes and lung gas volumes, not inferior to those of modified natural surfactants such as poractant alfa.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
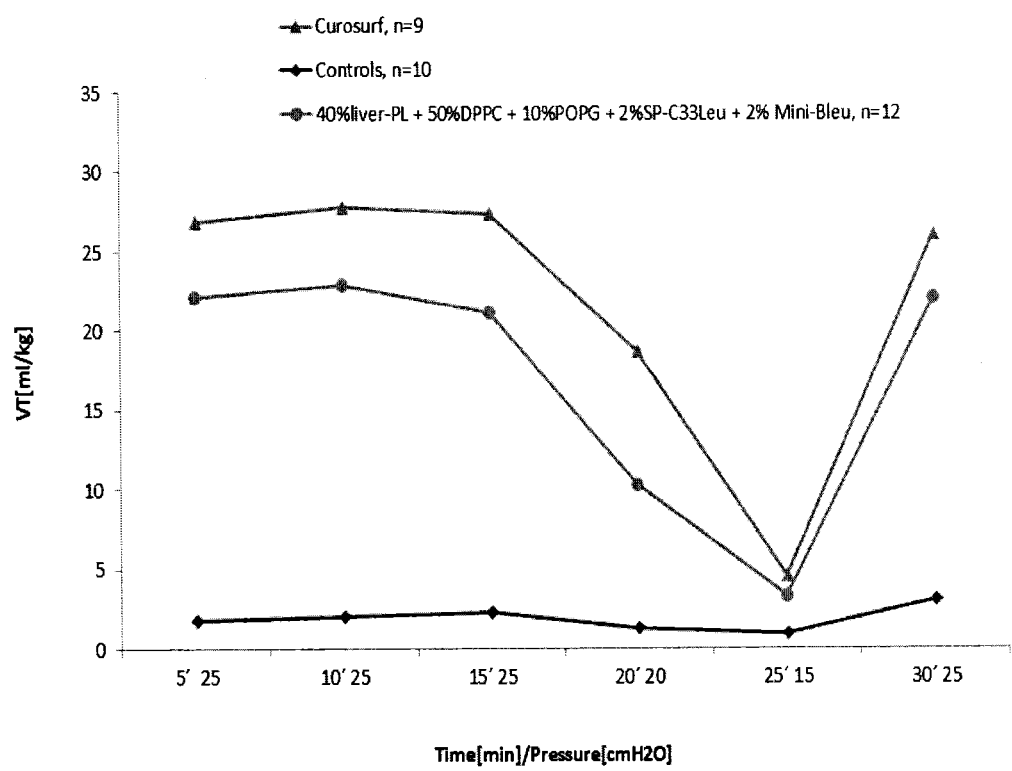
FIG. 1 shows the results in terms of tidal volumes (ml/kg) as a function of time/pressure of a reconstituted surfactant made of 2% ox Mini-B(Leu)+2% SP-C33(Leu)+50% DPPC+10% POPG+40% liver-PC versus Curosurf™ and controls.

In the present application, the term "reconstituted surfactant" means a lipid carrier to which polypeptide analogues of the surfactant proteins, made by any means including recombinant technology or synthetic methods, have been added.

The term "polypeptide analogues of the native surfactant protein SP-C" includes polypeptides having an amino acid sequence in which, compared to the native proteins, one or more amino acids are missing or have been replaced by other amino acids as long as the polypeptides, in a mixture with a lipid carrier, such as for example a phospholipid mixture, show pulmonary surfactant activity.

The term "polypeptide analogues of the native surfactant protein SP-B" includes peptides having an amino acid sequence in which, compared to the native proteins, one or more amino acids are missing or have been replaced by other amino acids as long as the polypeptides, in a mixture with a lipid carrier such as for example a phospholipid mixture, show pulmonary surfactant activity.

The term "mini-B" means a 34-residue polypeptide based on the N-terminal residues 8-25 and C-terminal residues 63-78 of the native SP-B protein whose structure was first generically disclosed in a presentation taken from the California NanoSystems Institute website. Its full sequence has been subsequently disclosed in the RCSB Protein Data Bank. In Waring A J et al J Peptide Res 2005, 66, 364-374, which is incorporated herein by reference in its entirety, more information about its structure and activity was reported.

The term "variants" means polypeptides analogues of the Mini-B peptide having an amino acid sequence in which one or more amino acids have been replaced by other amino acids, so long as the peptides, in a mixture with a lipid carrier, retain the activity of Mini-B.

All the amino acid residues identified herein are in the natural L-configuration and the sequences identified herein are reported according to standard abbreviations for amino acid residues as shown in the following Table.

Table of Amino Acids.

| Amino Acid | Symbol | |
|---|---|---|
| | One-Letter | Three-Letter |
| Glycine | G | Gly |
| L-proline | P | Pro |
| L-isoleucine | I | Ile |
| L-leucine | L | Leu |
| L-tyrosine | Y | Tyr |
| L-cysteine | C | Cys |
| L-tryptophan | W | Trp |
| L-alanine | A | Ala |
| L-lysine | K | Lys |
| L-arginine | R | Arg |
| L-glutamine | Q | Gln |
| L-methionine | M | Met |
| L-serine | S | Ser |
| L-valine | V | Val |
| L-aspargine | N | Asn |
| L-aspartic acid | D | Asp |
| L-glutamic acid | E | Glu |
| L-histidine | H | His |
| L-threonine | T | Thr |

Table of Amino Acids.

| Amino Acid | Symbol | |
|---|---|---|
| | One-Letter | Three-Letter |
| L-phenylalanine | F | Phe |
| L-nor-leucine | nL | nLeu |

As used in the text, the term "phospholipids" refers to a class of lipids constituted of glycerol, a phosphate group, a neutral or zwitter-ionic moiety as the characterizing part; one exception to this rule is sphingomyelin, which is derived from sphingosine instead of glycerol. The glycerol moiety or the sphingosine residue can be esterified with long chain fatty acids ($C_{14}$-$C_{22}$) which in turn can be saturated (e.g. myristic, palmitic, and stearic acid), monounsaturated (e.g. oleic acid) or polyunsaturated (e.g. linoleic and arachidonic acid).

The phospholipid classes and species cited in the present application are listed in the following Table together with the used abbreviations.

Table of Phospholipids phospholipids: PLs;
phosphatidylcholine: PC;
phosphatidylethanolamine: PE;
phosphatidylglycerol: PG;
phosphatidylinositol: PI;
phosphatidylserine: PS;
sphingomyelin: SM;
1,2-dipalmitoyl-sn-glycero-3-phosphocholine, generally known as dipalmitoyl-phosphatidylcholine: DPPC;
1-palmitoyl-2-oleoyl-sn-glycero-3-phosphocholine generally known as palmitoyl-oleoyl-phosphatidylcholine: POPC;
1-palmitoyl-2-linoleoyl-sn-glycero-3-phosphocholine, generally known as palmitoyl-linoleoyl-phosphatidylcholine: PLPC;
1-palmitoleoyl-2-oleoyl-sn-glycero-3-phosphocholine, generally known as palmitoleoyl-oleoyl-phosphatidylcholine: P(:1)OPC;
1-stearoyl-2-oleoyl-sn-glycero-3-phosphocholine generally known as stearoyl-oleoyl-phosphatidylcholine: SOPC;
1-stearoyl-2-linoleoyl-sn-glycero-3-phosphocholine, generally known as stearoyl-linoleoyl-phosphatidylcholine: SLPC;
1-stearoyl-2-arachidonoyl-sn-glycero-3-phosphocholine, generally known as stearoyl-arachidonoyl-phosphocholine: SAPC;
1-palmitoyl-2-arachidonoyl-sn-glycero-3-phosphocholine, generally known as palmitoyl-arachidonoyl-phosphocholine: PAPC;
1,2-dioleoyl-sn-glycero-3-phosphocholine, generally known as dioleoyl-phosphatidylcholine: DOPC;
1-palmitoyl-2-docosahexaenoyl-sn-glycero-3-phosphocholine generally known as palmitoyl-docosahexaenoyl-phosphatidylcholine: PDPC;
1,2-dipalmitoyl-sn-glycero-3-phosphoethanolamine, generally known as dipalmitoyl-phosphatidylethanolamine: DPPE;
1-palmitoyl-2-linoleoyl-sn-glycero-3-phosphoethanolamine, generally known as palmitoyl-linoleoyl phosphatidylethanolamine: PLPE;
1-stearoyl-2-oleoyl-sn-glycero-3-phosphoethanolamine, generally known as stearoyl-oleoyl phosphatidylethanolamine: SOPE;
1-stearoyl-2-linoleoyl-sn-glycero-3-phosphoethanolamine, generally known as stearoyl-linoleoyl phosphatidylethanolamine: SLPE;
1-stearoyl-2-arachidonoyl-sn-glycero-3-phosphoethanolamine, generally known as stearoyl-arachidonoyl-phosphatidylethanolamine: SAPE;
1-linoleoyl-2-arachidonoyl-sn-glycero-3-phosphoethanolamine, generally known as linoleoyl-arachidonoyl-phosphatidylethanolamine: LAPE;
1,2-dilinoleoyl-sn-glycero-3-phosphoethanolamine, generally known as dilinoleoyl-phosphatidylethanolamine: DLPE;
1,2-dioleoyl-sn-glycero-3-phosphoethanolamine, generally known as dioleoyl-phosphatidylethanolamine: DOPE;
1-palmitoyl-2-oleoyl-sn-glycero-3-phosphoglycerol, generally known as palmitoyl-oleoyl-phosphatidylglycerol: POPG;
1,2-dioleoyl-sn-glycero-3-phosphoglycerol generally known as dioleoyl-phosphatidylglycerol: DOPG;

-continued

Table of Phospholipids 1,2-dipalmitoyl-sn-glycero-3-phospho-L-serine, generally known as dipalmitoyl-phosphatidylserine: DPPS;
1,2-dipalmitoyl-sn-glycero-3-phosphoglycerol, generally known as dipalmitoyl-phosphatidylglycerol: DPPG; and
N-palmitoyl-D-sphingosylphosphorylcholine: PSM.

The expression "consisting essentially of" means that the naturally-derived fraction of unsaturated phospholipids may comprise further components, each of them in a very low amount (lower than 0.1% w/w) and that does not substantially affect the activity and the properties of said fraction.

"Surfactant activity" for a surfactant preparation is defined as the ability to lower the surface tension.

The in vitro efficacy of exogenous surfactant preparations is commonly tested by measuring its capability of lowering the surface tension using suitable apparatus such as Wilhelmy Balance and Captive Bubble Surfactometer.

The in vivo efficacy of exogenous surfactant preparations is commonly tested by measuring the following parameters:
 i) the tidal volume, which is an index of the lung compliance;
 ii) the lung gas volume, which is an index of the alveolar air expansion or patency at the end of expiration, and hence of the capability of forming a stable phospholipid film in the alveoli at the end of expiration;
 iii) the alveolar volume density, which is the percentage of total volume of the alveoli in the lung. The percentage is calculated by taking the total volume of the alveoli, divided by the total lung volume (alveoli+tissue, excluding e.g. bronchioli, vessels) according to the method disclosed on paragraph 2.2.2 of Berggren P et al Respiration Physiology, 1999, 115, 45-33, which is incorporated herein by reference in its entirety. The value is similar to the lung gas volume which is measured for the whole lung while alveolar volume density is measured from histological sections.

"Therapeutically effective amount" as used herein refers to an amount of reconstituted surfactant capable of preventing, avoiding, reducing or eliminating the respiratory disease or disorders associated with the lack or dysfunction of endogenous surfactant.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein.

As used herein, the term "about" applied to a point value, indicates a variability of ±5%.

The present invention is directed to a reconstituted surfactant comprising a polypeptide analogue of the native surfactant protein SP-C of formula (I), a polypeptide analogue of the native surfactant protein SP-B of formula (II) or (III) and a phospholipid mixture comprising a naturally-derived fraction enriched in unsaturated phospholipids.

It has indeed been found that said reconstituted surfactants preparation have properties in terms of tidal volumes and lung gas volumes not inferior to those of modified natural surfactants such as poractant alfa.

In particular, it was found that, besides the proteinaceous components, the phospholipid composition as well is very important in stabilizing the alveoli at end-expiration in animals ventilated without positive end-expiratory pressure (PEEP).

Moreover, it was found that, using the claimed phospholipid mixture, it is possible to provide compositions with low viscosity even if an SP-B analogue of formula (III) is used, which is shorter than the analogues of formula (II), but they give rise to viscous preparations when mixed with simple phospholipid mixture of DPPC and POPG.

Advantageously, the polypeptide analogue of the SP-C protein is represented by the general formula (I):

(SEQ ID NO: 1)
IPSSPVHLKRLKLLLLLLLLILLLILGALLΩ$_p$G$_p$L$_p$ (I)

wherein:
 Ω is an amino acid selected from the group consisting of M or M oxidized on the sulfur atom, I, L, and nL, preferably L
 p is 0 or 1.

Examples of polypeptides of formula (I) are reported below:

(SEQ ID NO: 2)
IPSSPVHLKRLKLLLLLLLLILLLILGALLMGL    (Ia)

(SEQ ID NO: 3)
IPSSPVHLKRLKLLLLLLLLILLLILGALLIGL    (Ib)

(SEQ ID NO: 4)
IPSSPVHLKRLKLLLLLLLLILLLILGALLLGL    (Ic)

(SEQ ID NO: 5)
IPSSPVHLKRLKLLLLLLLLILLLILGALLnLGL   (Id)

(SEQ ID NO: 6)
IPSSPVHLKRLKLLLLLLLLILLLILGALL       (Ie)

(SEQ ID NO: 7)
IPSSPVHLKRLKLLLLLLLLILLLILGALLL      (If)

The polypeptide (Ia) has been also referred in the prior art to as SP-C33.

In a preferred embodiment of the invention the polypeptide of general formula (I) is the polypeptide (Ic), referred in the art as SP-C33(Leu).

The analogue of the protein SP-B could be selected from different polypeptides corresponding to portions of the native protein or variants thereof.

In an embodiment of the invention, the analog of the native protein SP-B is a polypeptide represented by the following general formula (II):

(SEQ ID NO: 8)
(FPθPLPY)$_f$CΔLCRALIKRIQAΩIPKGGRΩLPQLVCRLVLΦCS (II)

wherein:
 θ is an amino acid residue selected from the group consisting of L, I and C, preferably C; and
 Δ is an amino acid residue selected from the group consisting of W, I and L, preferably W;
 Ω is an amino acid residue independently selected from the group consisting of M, I, L, and nL, preferably L;

Φ is an amino acid residue selected from the group consisting of R and T, preferably R; and f is 0 or 1.

Polypeptides according to general formula (II) in which f is 0 are reported below:

```
                                          (SEQ ID NO: 9)
CWLCRALIKRIQAMIPKGGRMLPQLVCRLVLRCS  (IIa)

(SEQ ID NO: 10)
CLLCRALIKRIQAMIPKGGRMLPQLVCRLVLRCS  (IIb)

(SEQ ID NO: 11)
CWLCRALIKRIQALIPKGGRLLPQLVCRLVLRCS  (IIc)

(SEQ ID NO: 12)
CLLCRALIKRIQALIPKGGRLLPQLVCRLVLRCS  (IId)
```

Preferably, the polypeptides (IIa), (IIb), (IIc) and (IId) may be in the form of a disulfide linked molecule wherein the intramolecular disulfide linkage is between the two C residues in positions 1 and 33 and/or between the two C residues in positions 4 and 27.

The disulfide linked polypeptide (IIa) has been referred in the art to as Mini-B and its disulfide linked form as oxidized Mini-B (ox Mini-B). See Waring A J et al J Peptide Res 2005, 66, 364-374, which is incorporated herein by reference in its entirety.

The polypeptide (IIc), which is particularly preferred, has been referred to in WO 2008/044109, which is incorporated herein by reference in its entirety, as Mini-B(Leu) and its disulfide linked form as ox Mini-B(Leu).

Polypeptides according to general formula (II) in which f is 1 are reported below:

```
                                              (SEQ ID NO: 13)
FPCPLPYCWLCRALIKRIQAMIPKGGRMLPQLVCRLVLRCS  (IIe)

(SEQ ID NO: 14)
FPIPLPYCWLCRALIKRIQAMIPKGGRMLPQLVCRLVLRCS  (IIf)

(SEQ ID NO: 15)
FPCPLPYCWLCRALIKRIQALIPKGGRLLPQLVCRLVLRCS  (IIg)

(SEQ ID NO: 16)
FPIPLPYCWLCRALIKRIQALIPKGGRLLPQLVCRLVLRCS  (IIh)
```

Preferably, said polypeptides may be in the form of a cyclic molecule wherein the linkage is between the C residues at positions 8 and 40 and/or between the C residues at positions 11 and 34.

In another embodiment of the invention, the analogue of the native protein SP-B is a polypeptide represented by the following general formula (III):

```
                                (SEQ ID NO: 17)
XΔLΩRALIKRFNRYLTPQLVΩRLVLRΦΣ_q  (III)
``` wherein

X is an amino acid residue selected from the group consisting of C, A and G, L, and I, preferably C;

Δ is an amino acid residue selected from the group consisting of W, L, nL and I, preferably W or L;

Φ is an amino acid residue selected from the group consisting of C, A and G, L, and I, preferably C;

Σ is an amino acid residue selected form the group consisting of S, G and A;

Ω is an aminoacid selected from the group consisting of C, L and I, preferably C and q is 0 or 1.

Advantageously, said polypeptides may be in the form of a cyclic molecule wherein the linkage is between the C residues at positions 1 and 27 and/or between the C residues at positions 4 and 21.

Polypeptides encompassed by general formula (III) are for example reported below:

```
                                    (SEQ ID NO: 18)
CLLCRALIKRFNRYLTPQLVCRLVLRC    (IIIa)

(SEQ ID NO: 18)
CWLCRALIKRFNRYLTPQLVCRLVLRC    (IIIb)

(SEQ ID NO: 20)
ALLCRALIKRFNRYLTPQLVCRLVLRAA   (IIIc)

(SEQ ID NO: 21)
GLLCRALIKRFNRYLTPQLVCRLVLRGG   (IIId)
```

Preferred polypeptide is that of formula (IIIb) in its disulfide linked form hereinafter referred as ox Mini-B27.

The polypeptides of general formulae (I), (II), and (III) may be prepared according to synthetic methods or recombinant techniques well known to the person skilled in the art.

An excellent summary of the many techniques available may be found in J. M. Steward and J. D. Young, "Solid Phase Peptide Synthesis," W.H. Freeman Co., San Francisco, 1969, and J. Meienhofer, Hormonal Proteins and Peptides", Vol. 2, p. 46, Academic Press (New York), 1983, both of which are incorporated herein by reference in their entireties, for solid phase peptide synthesis, and E. Schroder and K. Kubke, "The Peptides," Vol. 1, Academic Press (New York), 1965, which is incorporated herein by reference in its entirety, for classical solution synthesis. The polypeptides of the present invention can also be prepared using the solid-phase synthetic technique initially described by Merrifield, in J. Am. Chem. Soc. 85: 2149-2154 (1963), which is incorporated herein by reference in its entirety. Other polypeptide synthesis techniques may be found, for example, in M. Bodanszky et al., Peptide Synthesis, John Wiley & Sons, 2d Ed., (1976), which is incorporated herein by reference in its entirety, as well as in other reference works known to those skilled in the art.

Appropriate protective groups for use in such syntheses will be found in the above texts as well as in J. F. W. McOmie, Protective Groups in Organic Chemistry, Plenum Press, New York, N.Y. (1973), which is incorporated herein by reference in its entirety.

For example, the polypeptides of general formula (I) may be prepared according to the method disclosed in WO 00/47623, which is incorporated herein by reference in its entirety.

The polypeptides of general formula (II) wherein f is 0 may be prepared according to the methods reported in Waring A J et al J Peptide Res 2005, 66, 364-374 or in WO 2008/044109, which are incorporated herein by reference in their entireties, while the polypeptides of general formula (II) wherein f is 1 may be prepared according to the teaching of WO 2008/011559, which is incorporated herein by reference in its entirety The polypeptides of general formula (III) may prepared according to the methods disclosed in WO 2009/018908, which is incorporated herein by reference in its entirety.

The invention also includes the pharmaceutically acceptable salts of the polypeptides of general formulae (I), (II), and (III) and their blocked N- and/or C-terminus derivatives, e.g. via acetylation and amidation.

Pharmaceutically acceptable salts include for example, salts of hydrochloric acid, acetic acid, and trifluoroacetic acid.

The phospholipid POPG may advantageously be present in the form of pharmaceutically acceptable salts, for example as sodium salt (POPG Na).

Preferably, the polypeptides of general formula (I) and the polypeptides of general formula (II) or (III) are present in the reconstituted surfactants of the invention in a fixed amount and quantitative ratio as a fixed combination.

The proportion of the polypeptides of general formulae (I) and (II) or (III) relative to the reconstituted surfactant may vary. Advantageously each polypeptide may be present in an amount of 0.5 to 10% based on the weight of the surfactant (w/w), preferably 1 to 5%, most preferably 1 to 3%.

The phospholipid mixture consists of i) an amount of 50% by weight of DPPC; ii) an amount of 10% by weight of POPG; and iii) an amount of 40% by weight of a naturally-derived fraction of unsaturated phospholipids all the amounts i), ii) and iii) being calculated on the total weight of the phospholipid mixture.

In turn, the naturally-derived fraction of unsaturated phospholipids consists essentially of from 30 to 50% of POPC, from 10 to 20% of PLPC, from 4 to 10% of P(:1)OPC, from 5 to 8% of SLPC, from 5 to 8% of DOPC, from 1 to 3% of SAPC, from 5 to 15% of SOPC, from 1 to 2% of PAPC, from 1 to 3% of PDPC, from 0 to 3.5% of OPE, from 0 to 8% of SAPE, from 0 to 4% of SLPE, from 0 to 2.5% of PLPE, from 0 to 3.5% of POPE; from 0 to 2.0% of LAPE, from 0 to 2.% of LLPE, and from 0 to 10% of PSM;

The sum of the relative amounts of the different components constituting said fraction should be 100%. Their absolute amount based on the total weight of the phospholipid mixture could be calculated by multiplying each value by 0.4.

A typical composition the naturally-derived fraction of unsaturated phospholipids may be constituted of about 45% POPC, about 20% PLPC, about 6% P(:1)OPC, about 6% SLPC, about 6% DOPC, about 3% SAPC, about 10% SOPC, about 2% PAPC, and about 2% PDPC, based on the weight of the L-α-phosphatidylcholine extract.

Another typical composition of said fraction may be constituted of about 35% POPC, about 20% PLPC, about 5% P(:1)OPC, about 5% SLPC, about 5% DOPC, about 1% SAPC, about 7% SOPC, about 1% PAPC, about 1% PDPC, about 2% SOPE, about 7% SAPE, about 3% SLPE, about 2% PLPE, about 2% POPE; about 2% LAPE, about 1% LLPE, and about 1% PSM based on the weight of the L-α-phosphatidylcholine extract.

In one embodiment of the invention, as a source of naturally-derived fraction of unsaturated phospholipids, L-α-phosphatidylcholines derived from egg yolk having different purities may be used (Sigma Aldrich Co, St. Louis, Mo., USA).

For example, L-α-phosphatidylcholine derived from egg yolk having a purity of more than 99% w/w may advantageously be used. It has essentially the following composition: from 40 to 50% POPC, from 15 to 20% PLPC, from 5 to 7% P(:1)OPC, from 6 to 7% SLPC, from 6 to 7% DOPC, from 2 to 3% SAPC, from 10 to 15% SOPC, from 1 to 2% PAPC, and from 1 to 2% PDPC, based on the weight of the L-α-phosphatidylcholine extract.

Otherwise, L-α-phosphatidylcholine derived from egg yolk having a purity of about 40% w/w may be utilized, that has the following composition: from 30 to 40% POPC, from 13 to 18% PLPC, from 3 to 4% P(:1)OPC, from 5 to 6% SLPC, from 5 to 6% DOPC, from 1 to 2% SAPC, from 6 to 8% SOPC, from 1 to 2% PAPC, from 1 to 2% PDPC, from 3 to 3.5% SOPE, from 7 to 8% SAPE, from 3.5 to 4.5% SLPE, from 2 to 2.5% PLPE, from 3 to 3.5% POPE; from 1.5 to 2.0% LAPE, from 1 to 2% LLPE, and from 0.5 to 1% PSM, based on the weight of the L-α-phosphatidylcholine extract.

As a source of the fraction of unsaturated phospholipids, L-α-phosphatidylcholine derived from bovine liver having a purity of more than 99% w/w could also be used. Alternatively, said fraction may be isolated from other sources, such as rabbit liver by chromatography according to methods known to the skilled person.

Theoretically, the fraction of unsaturated phospholipids may also be prepared by the skilled person in the art by mixing each component in a suitable amount.

The relative amounts of phospholipid may be determined according to methods known in the art, for instance by LC-MS according to the method reported on Miroslav L et al J Chromatog A 2011, 1218, 5146-5156, which is incorporated herein by reference in its entirety.

In particular embodiments of the invention, the reconstituted surfactant may comprise further components, for example neutral lipids such as triacylglycerols, free fatty acids, cholesterol and/or further phospholipids such as lyso-phosphatidylcholines, lysophosphatidylethanolamines, DPPS and DPPG, and DOPE.

Advantageously, the reconstituted surfactant according to the present invention comprises 90 to 99% by weight of the phospholipid mixture, preferably 92 to 98%, more preferably 94 to 96%, and 1 to 10% by weight of the sum of a peptide of formula (I) and a peptide of formula (II), (III) or (IV), preferably 2 to 8%, more preferably 4 to 6%.

In one of the embodiments of the present invention, the reconstituted surfactant comprises 96% by weight of the phospholipid mixture, 2% by weight of a polypeptide of general formula (I) and 2% by weight of a polypeptide of general formula (II).

In another embodiment, the reconstituted surfactant comprises 96% by weight of the phospholipid mixture, 2% by weight of a polypeptide of general formula (I) and 2% by weight of a polypeptide of general formula (III).

Effective doses of the reconstituted surfactant of the invention for the treatment of a disease such as RDS, as described herein, vary depending upon many different factors, including type of the disease, means of administration, weight and physiological state of the patient, and whether treatment is prophylactic or therapeutic.

In general, the dose is from 0.01 mg to 10 g per kg of body weight, preferably from 0.1 to 1 g per kg of body weight and the frequency of administration can vary depending on whether the treatment is prophylactic or therapeutic. Typically a dose of about 50 mg/kg, 100 mg/kg, or 200 mg/kg are administered in one dose. For use in newborns, one or two administrations are generally sufficient.

Although needs can vary depending on the severity of the respiratory disease and/or other variables, the determination of the optimal ranges for effective dosages is within the knowledge of the skilled person in the art.

The present invention also concerns pharmaceutical formulations comprising the reconstituted surfactant of the invention.

Said formulations are advantageously administered in the form of a solution, dispersion, suspension or dry powder. Preferably said compositions comprise the reconstituted surfactant dissolved or suspended in a suitable physiologically tolerable solvent or re-suspension carrier, such as water or a physiological saline aqueous solution (0.9% w/v NaCl).

The formulations of the present invention are preferably in form of suspension in an aqueous solution, more preferably sterile, which may optionally comprise pH buffering agents, diluents and other suitable additives.

Advantageously the viscosity of said formulations is less than 20 centiPoise (cP), preferably less than 15 cP, upon determination with a common viscometer available on the market according to methods known in the art.

The formulations may be presented in unit-dose or multi-dose containers, for example sealed ampoules and vials, or may be stored in a frozen or freeze-dried (lyophilized) condition requiring only the addition of sterile liquid carrier immediately prior to use.

Preferably the reconstituted surfactant of the invention is supplied as sterile suspension in a buffered physiological saline aqueous solution in single-use glass vials.

The pharmaceutical formulations may be prepared according to conventional techniques well known in the pharmaceutical industry. Such techniques include the step of admixing the polypeptides and the phospholipids in the presence of an organic solvent. The solvent is then removed by dialysis or evaporation under nitrogen and/or exposure to vacuum or by other appropriate techniques well known to the skilled person in the art, such as lyophilisation and spray-drying.

The obtained powder is then uniformly and intimately brought into association with liquid carriers or finely divided solid carriers or both.

The mixture of polypeptides and phospholipids can be sterilized before removing the solvent for example by sterile filtration. In certain other embodiments, the reconstituted surfactant composition is terminally sterilized according to methods well known in the art.

The administration of the reconstituted surfactant of the invention is carried out in a manner known to the person skilled in the art, e.g. by intratracheal installation (infusion or bolus or through a catheter), by spray administration, or nebulization.

As disclosed herein, the invention contemplates the use of both concentrated and dilute surfactant formulations, depending upon the particular use, as described further herein. Concentrated surfactant compositions are typically used for "bolus" type administrations, whereas dilute surfactant compositions are typically used for "lavage" type administrations.

Advantageously, for "bolus" type administration, the reconstituted surfactant concentration in terms of weight per ml of solution or suspension (following addition of a liquid carrier) is in the range of from 5 to 100 mg/ml, preferably between 20 and 80 mg/ml.

In a preferred embodiment of the invention, when the reconstituted surfactant is administered by intratracheal instillation as a suspension in physiological saline (0.9% w/v sodium chloride in water), the concentration is of about 80 mg/ml.

When used for lavage administration, a typical surfactant concentration is from about 0.1 to 20 mg/ml, and more preferably about 0.5 to 10 mg/ml (in terms of mg surfactant per ml of solution or suspension).

Since it depends on the concentration, the viscosity of diluted formulations would be even lower.

When used as a pharmaceutical treatment, the formulations comprising the reconstituted surfactant of the present invention may be administered either alone or optionally in conjunction with other compounds or compositions that are used in the treatment of respiratory diseases or disorders. For example, if a subject is being treated for a respiratory disorder caused by a bacterial infection, then the reconstituted surfactant of the present invention may be administered in conjunction with another compound used to treat the bacterial infection, such as an antibiotic.

Otherwise, in certain cases, for example for preventing complications such as bronchopulmonary dysplasia, the reconstituted surfactant of the present invention may be administered in conjunction with corticosteroids such as budesonide and beclometasone dipropionate.

In certain embodiments, the reconstituted surfactant of the present invention and the re-suspension carrier may be separately packed at the same time in a suitable container mean. Such separate packaging of the components in a suitable container mean is also described as a kit.

Therefore, this invention is also directed to a kit, comprising: a) the reconstituted surfactant of the invention in a powder form in a first unit dosage form; b) a pharmaceutically acceptable carrier in a second unit dosage form; and c) container means for containing said first and second dosage forms.

Preferably, the pharmaceutically acceptable carrier is a physiological saline aqueous solution, more preferably sterile.

As disclosed herein, a variety of methods for administering the reconstituted surfactant and formulations thereof of the present invention are available and are well known by one of skill in the art.

Depending on the type of disease e.g., an infant or adult with respiratory distress syndrome, different treatment methods can be appropriate.

Typically the surfactant is administered by endotracheal instillation to patients (e.g. pre-term infants) kept under continuous or intermittent positive pressure ventilation (IPPV).

Alternatively, the surfactant may be administered by the use of a thin catheter placed in the trachea and the patient respiration supported with specially designed nasal devices such as masks, prongs or tubes according to methodology known as nasal Continuous Positive Airway Pressure (nC-PAP).

The latter approach would be only possible with a surfactant having low viscosity as a high viscosity would make the passage of the surfactant through the thin catheter more difficult.

In instances in which the patient suffers from a respiratory distress condition associated with pulmonary inflammation, pulmonary infection or pulmonary contusion, particular treatment modalities can be recommended. In one such therapeutic method, lavage of the patient's lungs with a surfactant composition of the present invention is performed as a single or multiple treatments.

The reconstituted surfactant of the invention is suitable to prevent, delay, alleviate, arrest or inhibit development of the symptoms or conditions associated with a respiratory disease.

In particular it is useful for the prophylaxis and/or treatment of respiratory distress syndrome (RDS) in prematurely born babies or other diseases related to a surfactant-deficiency or dysfunction including acute lung injury (ALI), RDS in adults (ARDS), meconium aspiration syndrome (MAS), and bronchopulmonary dysplasia (BPD).

It may also be useful for the prophylaxis and/or treatment of other respiratory disorders such as chronic obstructive pulmonary disease (COPD), asthma, respiratory infection (e.g. pneumonia, *pneumocystis carinii*, cystic fibrosis and respiratory syncytial virus) as well as for the treatment of serous otitis media (glue ear).

Other features of the invention will become apparent in the course of the following descriptions of exemplary embodiments which are given for illustration of the invention and are not intended to be limiting thereof.

EXAMPLES

Example 1

Preparation of the Reconstituted Surfactants

Materials:

The phospholipids 1,2-dipalmitoyl-sn-glycero-3-phosphocholine (DPPC), 1-palmitoyl-2-oleyl-sn-glycero-3-phosphoglycerol (POPG), L-α-phosphatidylcholines derived from egg yolk having purities higher than 99% a yolk (hereinafter pure egg yolk-PC) and of about 40% (hereinafter not purified egg yolk-PC), were purchased. The phosphatidylcholine fraction derived from rabbit liver (hereinafter liver-PC) was isolated by a chromatography on Lipidex-5000 as reported in Curstedt T., Analysis of molecular species of ether analogues of phosphatidylcholines from biological samples, Biochim Biophys Acta 1977; 489:79-88, which is incorporated herein by reference in its entirety. The polypeptides SP-C33(Leu) and ox-Mini-B(Leu) were prepared as disclosed in WO 2008/044109, which is incorporated herein by reference in its entirety, while the polypeptide ox Mini-B27 was prepared as disclosed in WO 2009/018908, which is incorporated herein by reference in its entirety.

Preparation of the Reconstituted Surfactants:

The phospholipids, dissolved in chloroform/methanol 98:2 (v/v), were mixed in the proportions DPPC:POPG:egg yolk-PC (liver-PC) 50:10:40 by weight. Corresponding reconstituted surfactant preparations (surfactant A and B) were prepared by adding each polypeptide in an amount of 2% by weight. The obtained surfactants were evaporated under nitrogen and re-suspended in 0.9% w/w NaCl aqueous solution at a concentration of 80 mg/ml.

Example 2

In Vivo Experiment with a Reconstituted Surfactant Made of 2% Ox Mini-B(Leu)+2% SP-C33(Leu)+50% DPPC+10% POPG+40% Liver-PL Immature newborn rabbits (gestational age 27 days) were treated at birth with 200 mg/kg of the reconstituted surfactant preparation (80 mg/ml). Animals receiving the same dose of poractant alfa (Curosurf™) served as positive and non-treated littermates as negative controls. The newborn rabbits were ventilated in parallel with a standardized sequence of peak insufflation pressures. To open up the lungs, pressure was first set at 35 cmH$_2$O for 1 minute. After this recruitment manoeuvre, pressure was lowered to 25 cmH$_2$O for 15 minutes and further on to 20 and 15 cm H$_2$O. Finally, pressure was raised again to 25 cmH$_2$O for 5 minutes, after which the lungs were ventilated for additional 5 minutes with nitrogen and then excised for gas volume measurements. The experiments were performed without PEEP. Both tidal volumes and lung gas volumes are given as median values.

The lungs were fixed by immersion in 4% neutral formalin, dehydrated and embedded in paraffin. Transverse sections were stained with hematoxylin and eoxin. Alveolar volume density was measure with a computer-aided image analyzer using total parenchyma as reference volume.

Figure 2:
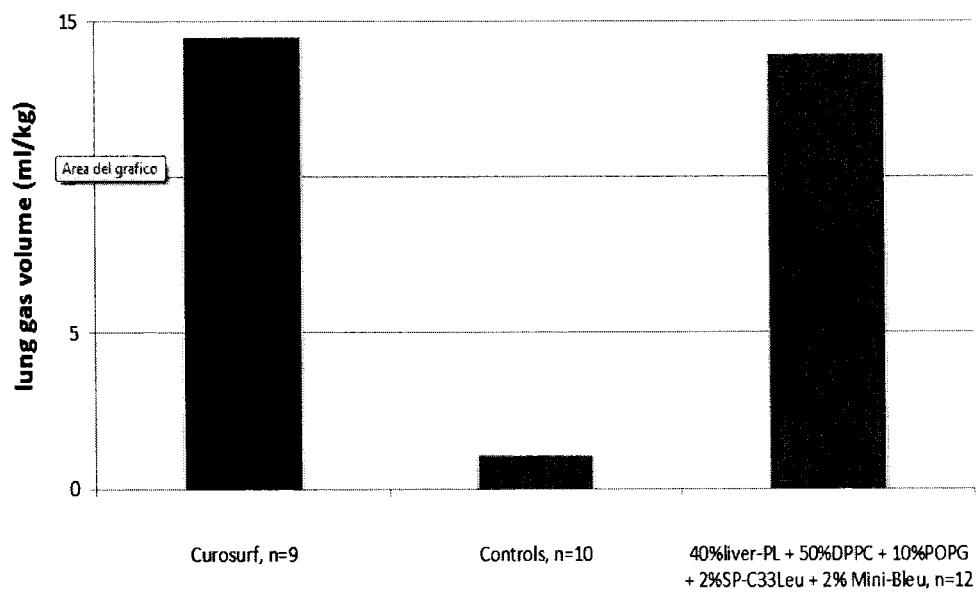
FIG. 2 shows the results in terms of lung gas volumes (ml/kg) of a reconstituted surfactant made of 2% ox Mini-B (Leu)+2% SP-C33(Leu)+50% DPPC+10% POPG+40% liver-PC versus Curosurf™ and controls.

The results indicate that the a reconstituted surfactant comprising a phospholipid mixture based on liver-PL and DPPC and POPG as synthetic phospholipids, 2% each of SP-C33Leu and ox Mini-B(Leu) gave similar tidal volumes (see FIG. 1) and lung gas volumes (see FIG. 2) as Curosurf™. Moreover, from Table 1, it can be appreciated that the reconstituted surfactant gave a similar alveolar volume density as Curosurf™ and significantly higher that the mixture of phospholipids only.

TABLE 1

Alveolar volume density (%) in preterm rabbits.

| | n | Alveolar volume density (%) |
|---|---|---|
| 2% SP-C33Leu + 2% Mini-Bleu 40% liver-PL + 50% DPPC + 10% POPG | 10 | 64** |
| Only phosholipids | 12 | 43 |
| Curosurf ™ | 10 | 61# |
| Non-treated controls | 11 | 40 |

**p < 0.002-0.0002 vs all groups except Curosurf ™
p < 0.02-0.0002 vs all groups except the reconstituted surfactant Example 3

Figure 3:
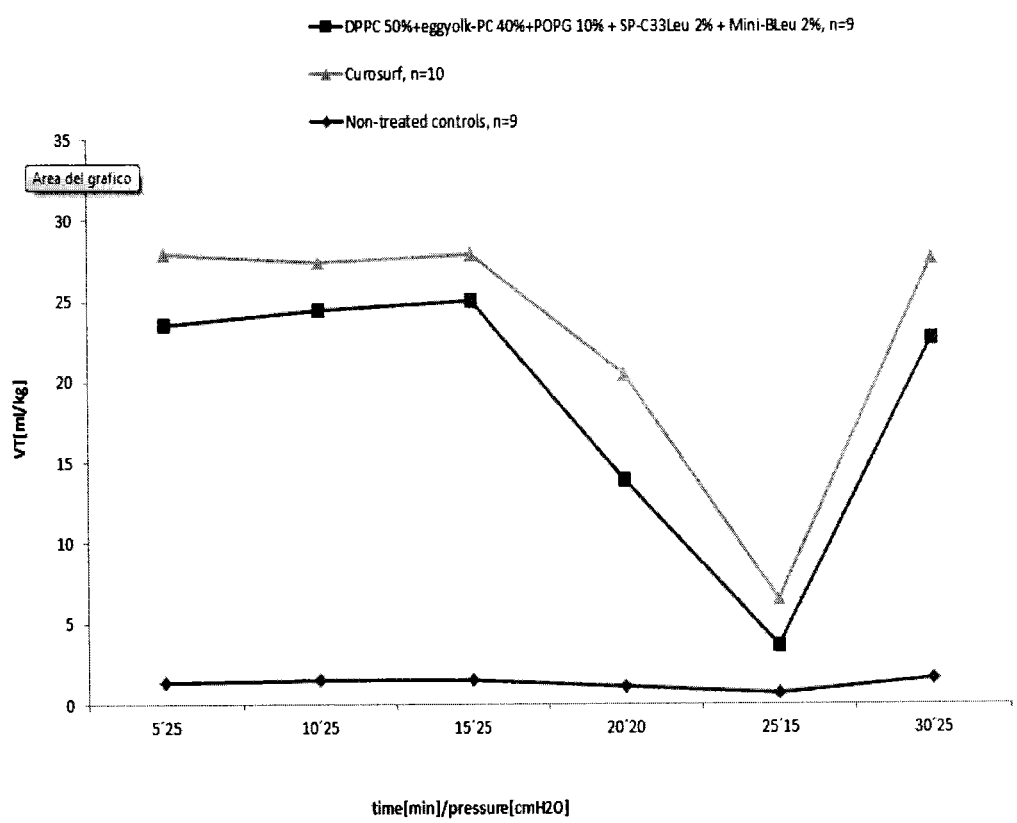
FIG. 3 shows the results in terms of tidal volumes (ml/kg) as a function of time/pressure of a reconstituted surfactant made of 2% ox Mini-B(Leu)+2% SP-C33(Leu)+50% DPPC+10% POPG+40% not purified egg yolk-PC versus Curosurf™ and controls.
Figure 4:
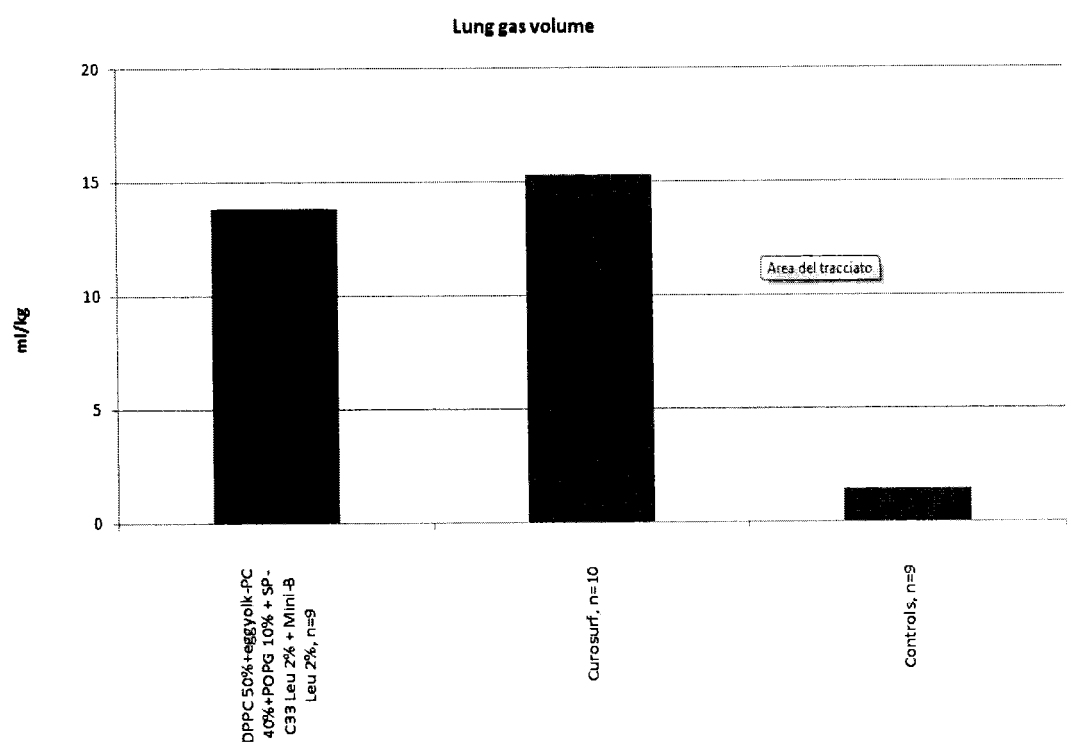
FIG. 4 shows the results in terms of lung gas volumes (ml/kg) of a reconstituted surfactant made of 2% ox Mini-B (Leu)+2% SP-C33(Leu)+50% DPPC+10% POPG+40% not purified egg yolk-PC versus Curosurf™ and controls.

In Vivo Experiment with a Reconstituted Surfactant Made of 2% ox Mini-B(Leu)+2% SP-C33(Leu)+50% DPPC+10% POPG+40% Not Purified Egg Yolk-PC The experiment was carried out as described in Example 2. Both tidal volumes and lung gas volumes are reported in FIGS. 3 and 4 as median values. The results indicate that also a reconstituted surfactant comprising a phospholipid mixture containing 50% DPPC, 40% egg yolk-PC and 10% POPG had similar tidal volumes and lung gas volumes as Curosurf™.

Example 4

Figure 5:
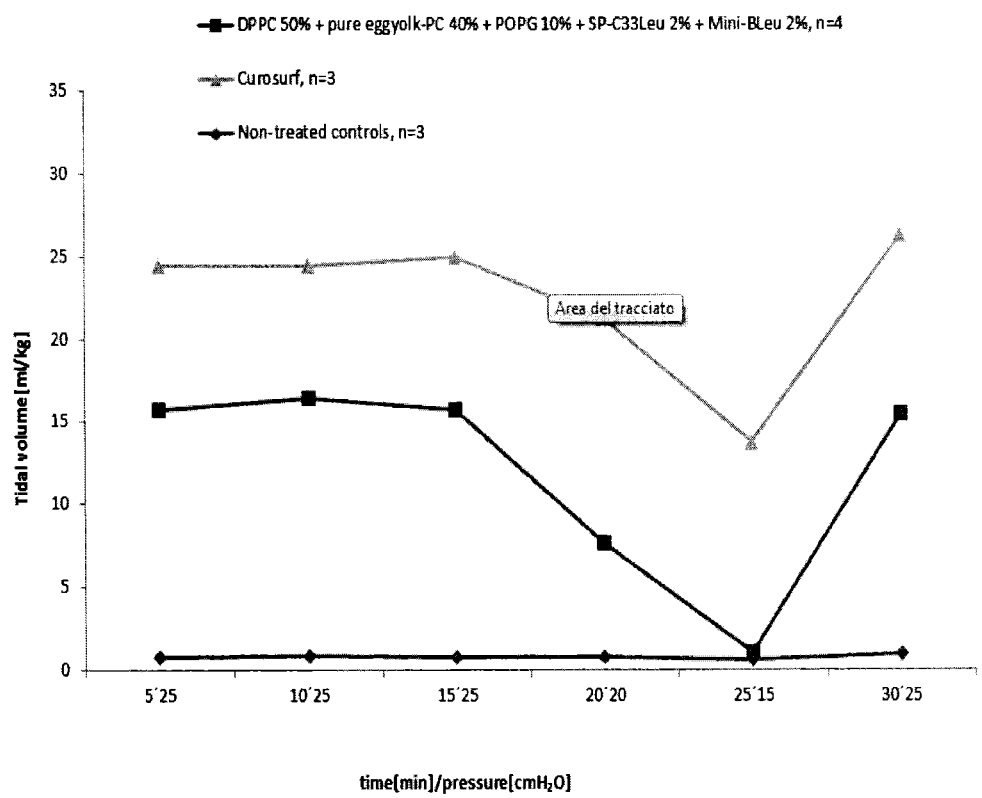
FIG. 5 shows the results in terms of tidal volumes (ml/kg) as a function of time/pressure of a reconstituted surfactant made of 2% ox Mini-B(Leu)+2% SP-C33(Leu)+50% DPPC+10% POPG+40% pure egg yolk-PC versus Curosurf™ and controls.
Figure 6:
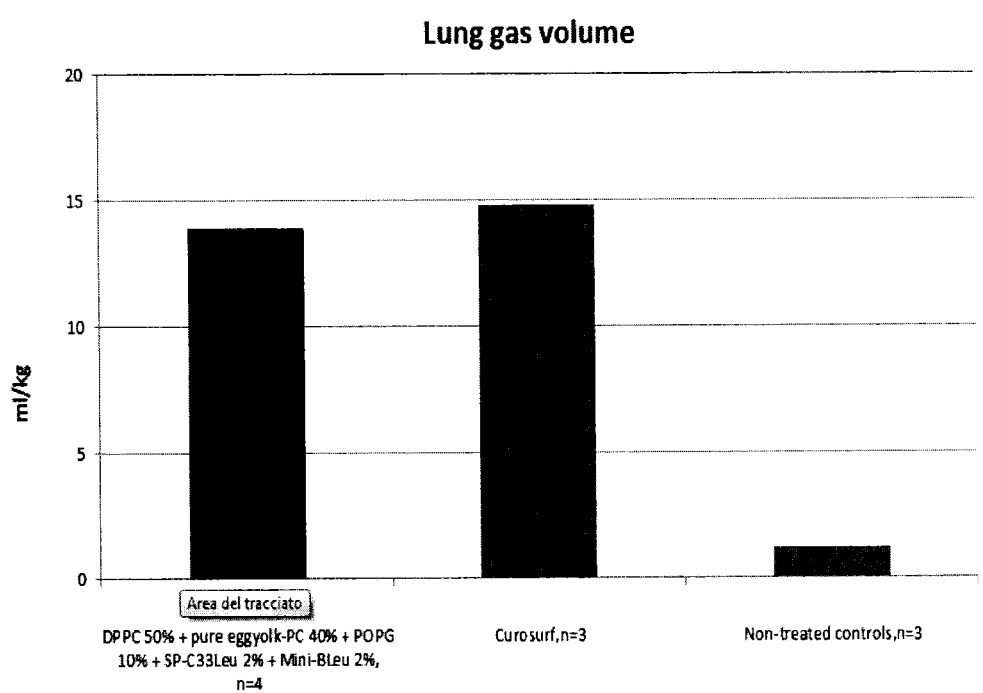
FIG. 6 shows the results in terms of lung gas volumes (ml/kg) of a reconstituted surfactant made of 2% ox Mini-B (Leu)+2% SP-C33(Leu)+50% DPPC+10% POPG+40% pure egg yolk-PC versus Curosurf™ and controls.

In Vivo Experiment with a Reconstituted Surfactant Made of 2% ox Mini-B(Leu)+2% SP-C33(Leu)+50% DPPC+10% POPG+40% Pure Egg Yolk-PC The experiment was carried out as described in Example 2. Both tidal volumes and lung gas volumes are reported in FIGS. 5 and 6 as median values. The results indicate that even though pure egg yolk-PC is used, the corresponding reconstituted surfactant had similar lung gas volumes as Curosurf™ but somewhat, not significantly, smaller tidal volumes.

Example 5

Figure 7:
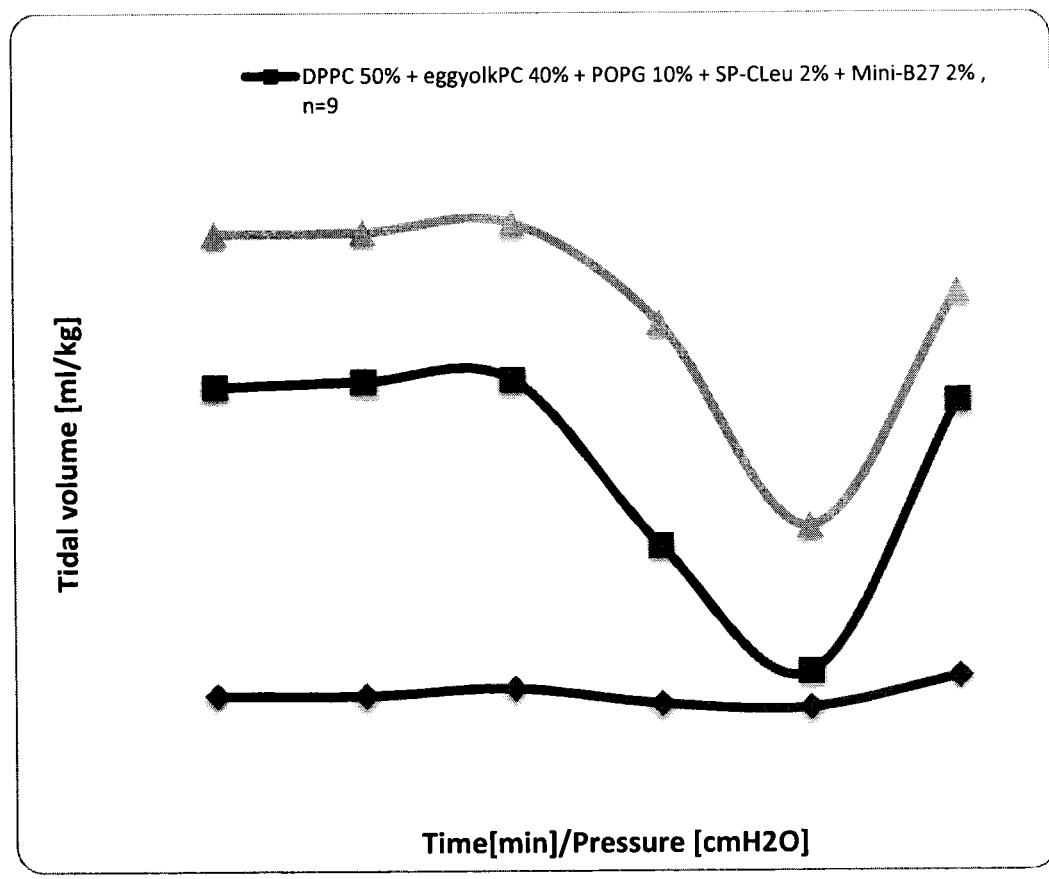
FIG. 7 shows the results in terms of tidal volumes (ml/kg) as a function of time/pressure of a reconstituted surfactant made of 2% ox Mini-B27+2% SP-C33(Leu)+50% DPPC+10% POPG+40% pure egg yolk-PC versus Curosurf™ and controls.
Figure 8:
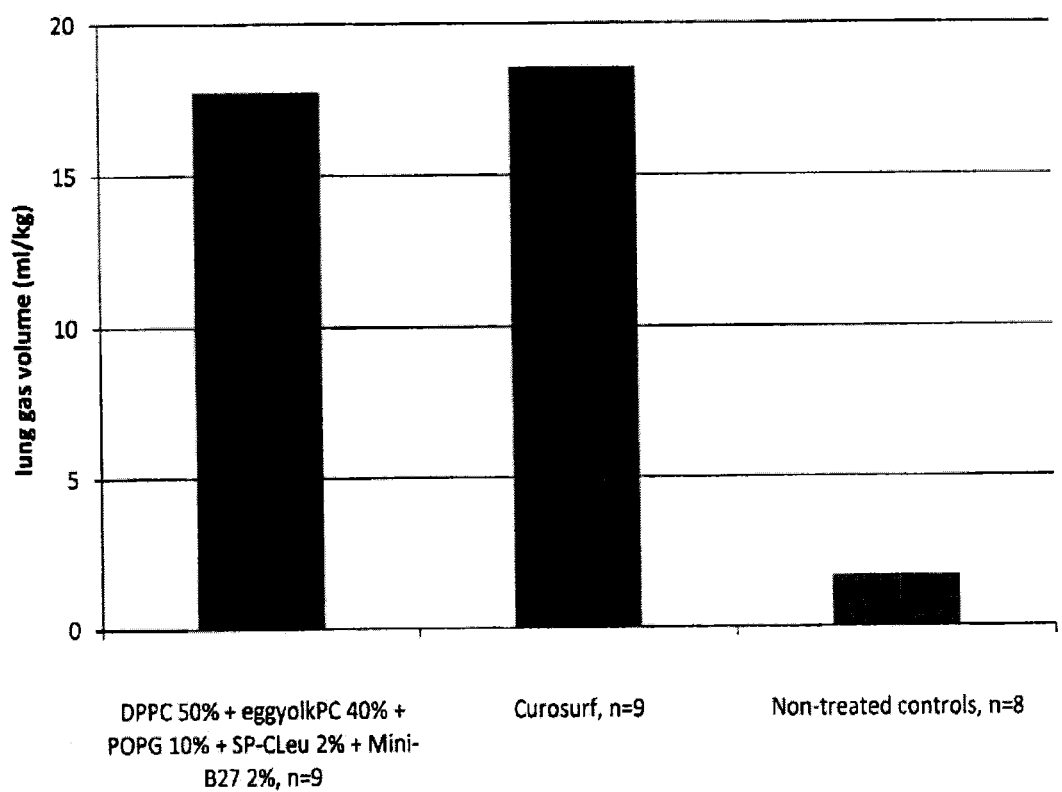
FIG. 8 shows the results in terms of lung gas volumes (ml/kg) of a reconstituted surfactant made of 2% ox Mini-B27+2% SP-C33(Leu)+50% DPPC+10% POPG+40% pure egg yolk-PC versus Curosurf™ and controls.

In Vivo Experiment with a Reconstituted Surfactant Made of 2% ox Mini-B27+2% SP-C33(Leu)+50% DPPC+10% POPG+40% Pure Egg Yolk-PC The experiment was carried out as described in Example 2. However, as SP-B analogue, the polypeptide quoted as ox Mini-B27 instead of ox Mini-B(Leu) was used. This is a shorter analogue of ox Mini-B(Leu), but said polypeptide gives rise to a viscous preparation when mixed with a phospholipid mixture consisting of DPPC:POPG 7:3 (w/w). Both the obtained tidal volumes and lung gas volumes are reported in FIGS. 7 and 8 as median values. Said reconstituted surfactant gave rise to somewhat smaller tidal volumes than Curosurf™, but the lung gas volumes were similar. Moreover, the corresponding formulation in form of aqueous suspension at 80 mg/ml had a low viscosity.

Example 6

In Vivo Experiment with Constant Tidal Volumes

Immature newborn rabbits (gestational age 27 days) were treated at birth with 200 mg/kg of different surfactant preparations (80 mg/ml). Animals receiving the same dose of Curosurf™ served as positive and non-treated littermates as negative controls. The newborn rabbits were ventilated in parallel with individual pressures in order to obtain standardized tidal volumes. A constant tidal volume of 6 ml/kg was used. To open up the lungs, pressure was first set at 35 cmH$_2$O for 1 minute. After this recruitment manoeuvre, pressure was lowered to keep tidal volumes for 30 min between 6-8 ml/kg. The experiments were performed without PEEP.

Figure 9:
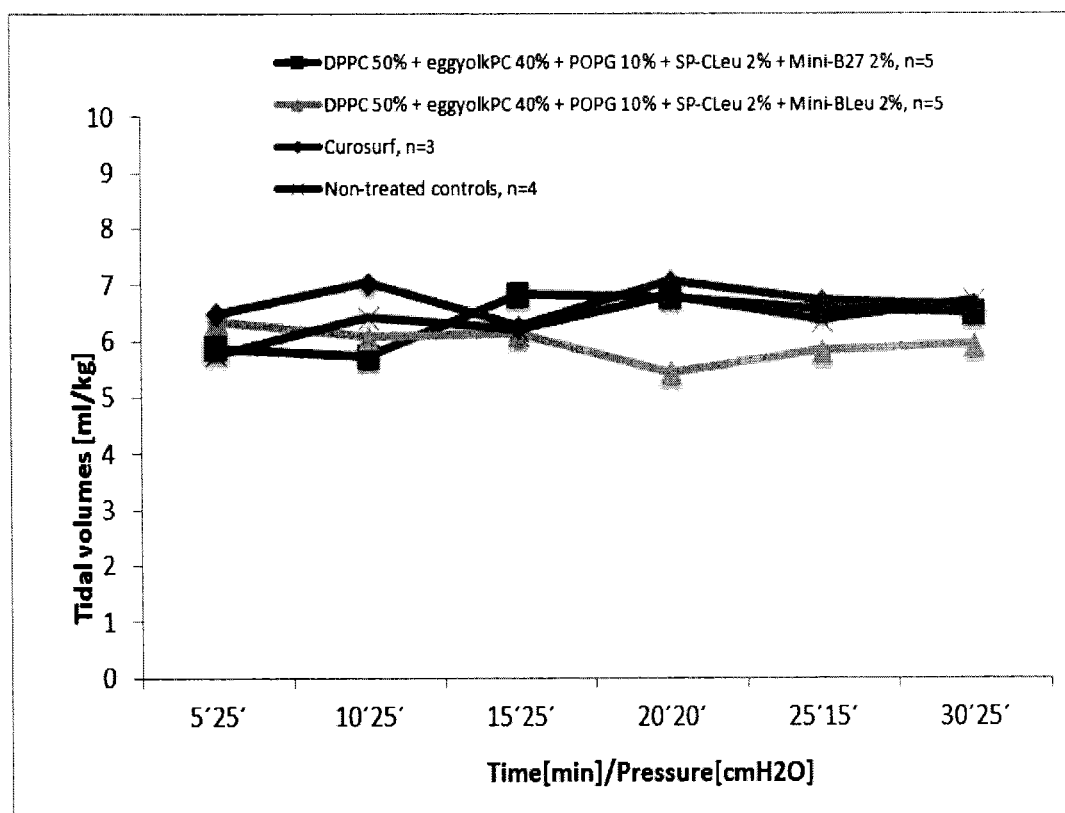
FIG. 9 shows the results in terms of tidal volumes (ml/kg) in the experiment carried out at constant tidal volume of reconstituted surfactants made of 2% ox Mini-B(Leu) or ox Mini-B27+2% SP-C33(Leu)+50% DPPC+10% POPG+40% pure egg yolk-PC versus Curosurf™ and controls.
Figure 10:
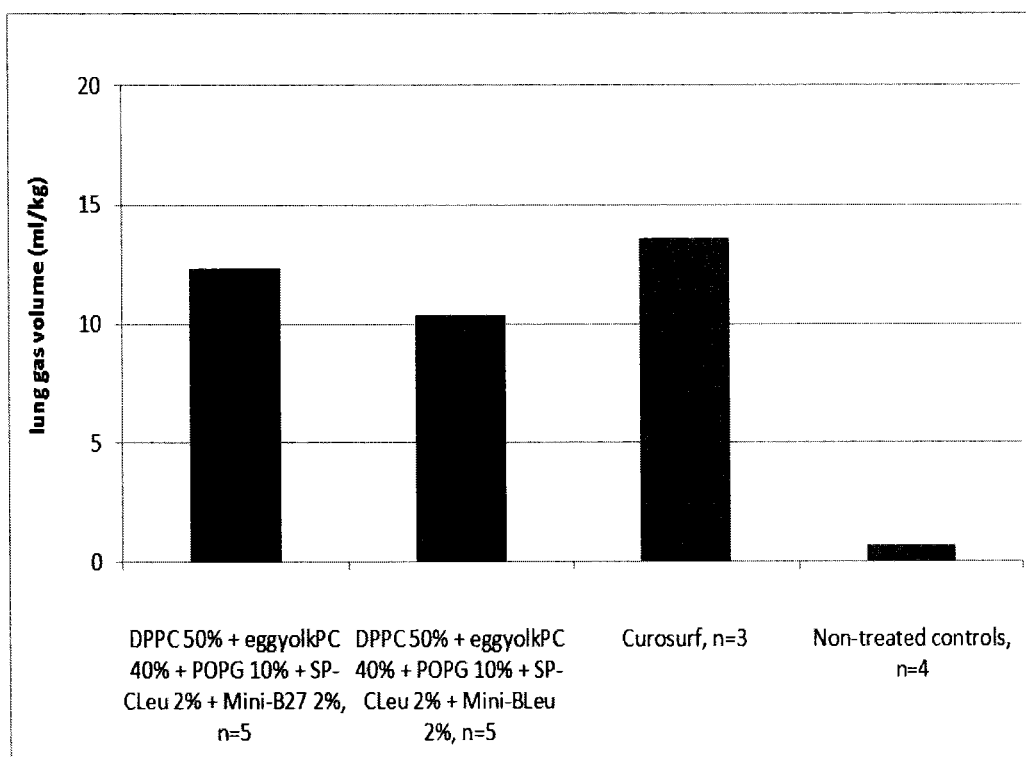
FIG. 10 shows the results in terms of lung gas volumes (ml/kg) in the experiment carried out at constant tidal volume of reconstituted surfactants made of 2% ox Mini-B(Leu) or ox Mini-B27+2% SP-C33(Leu)+50% DPPC+10% POPG+40% pure egg yolk-PC versus Curosurf™ and controls.

The following samples were tested:
1. DPPC 50%+eggyolkPC 40%+POPG 10%+SP-C33Leu 2%+Mini-B27 2%
2. DPPC 50%+eggyolkPC 40%+POPG 10%+SP-C33Leu 2%+Mini-BLeu 2%
3. Curosurf™
4. Non-treated controls Both tidal volumes and lung gas volumes are reported as median values in FIGS. 9 and 10. It appears that the reconstituted surfactant preparations containing Mini-B27 or Mini-BLeu had similar lung gas volumes as animals treated with Curosurf™ in experiments when the animals were ventilated with physiological tidal volumes (about 6 ml/kg) without PEEP.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A reconstituted surfactant, comprising:
   (a) a phospholipid mixture;
   (b) a polypeptide analogue of the native surfactant protein SP-B; and
   (c) a polypeptide analogue of the native surfactant protein SP-C represented by formula (I):

IPSSPVHLKRLKLLLLLLLLILLLILGALLΩ$_p$G$_p$L$_p$     (SEQ ID NO: 1) (I)

in which:
   Ω is M or M oxidized on the sulfur atom, I, L, or nL;
   p is 0 or 1
   wherein said phospholipid mixture consists of:
   i) about 50% by weight of DPPC;
   ii) about 10% by weight of POPG; and
   iii) about 40% by weight of a naturally-derived fraction of unsaturated phospholipids essentially consisting of:
      from 30 to 50% by weight of POPC;
      from 10 to 20% by weight of PLPC;
      from 4 to 10% by weight of P(:1)OPC;
      from 5 to 8% by weight of SLPC;
      from 5 to 8% by weight of DOPC;
      from 1 to 3% by weight of SAPC;
      from 5 to 15% by weight of SOPC;
      from 1 to 2% by weight of PAPC;
      from 1 to 3% by weight of PDPC;
      from 0 to 3.5% by weight of SOPE;
      from 0 to 8% by weight of SAPE;
      from 0 to 4% by weight of SLPE;
      from 0 to 2.5% by weight of PLPE;
      from 0 to 3.5% by weight of POPE;
      from 0 to 2.0% by weight of LAPE;
      from 0 to 2.% by weight of LLPE; and
      from 0 to 10% by weight of PSM;
   all the amounts i), ii) and iii) being calculated on the total weight of the phospholipid mixture,
   wherein said polypeptide analogue of the native surfactant protein SP-B is represented by formula (II):

(FPθPLPY)$_f$CΔLCRALIKRIQAΩIPKGGRΩLPQLVCRLVLΦCS (SEQ ID NO: 8) (II)

wherein:
   θ is L, I or C;
   Δ is W, I or L;
   Ω is M, I, L, or nL;
   Φ is R or T; and
   f is an integer having a value of 0 or 1,
   which, when f is 0, may be in the form of a disulfide linked molecule wherein the intramolecular disulfide linkage is between the two C residues in positions 1 and 33 and/or between the two C residues in positions 4 and 27, or
   which, when f is 1, may be in the form of a disulfide linked molecule wherein the linkage is between the C residues at positions 8 and 40 and/or between the C residues at positions 11 and 34.

2. A reconstituted surfactant according to claim 1, wherein said polypeptide analogue of the native surfactant protein SP-C has the sequence represented by formula (Ic):

IPSSPVHLKRLKLLLLLLLLILLLILGALLLGL (Ic).     (SEQ ID NO: 4)

3. A reconstituted surfactant according to claim 1, wherein said polypeptide analogue of formula (II) is represented by formula (IIa), formula (IIb), formula (IIc), or formula (IId):

CWLCRALIKRIQAMIPKGGRMLPQLVCRLVLRCS (IIa)     (SEQ ID NO: 9)
   CLLCRALIKRIQAMIPKGGRMLPQLVCRLVLRCS (IIb)     (SEQ ID NO: 10)
   CWLCRALIKRIQALIPKGGRLLPQLVCRLVLRCS (IIc)     (SEQ ID NO: 11)
   CLLCRALIKRIQALIPKGGRLLPQLVCRLVLRCS (IId),     (SEQ ID NO: 12)

which may be in the form of a disulfide linked molecule wherein the intramolecular disulfide linkage is between the two C residues in positions 1 and 33 and/or between the two C residues in positions 4 and 27.

4. A reconstituted surfactant according to claim 1, wherein said polypeptide of formula (II) is represented by formula (IIe), formula (IIf), formula (IIg), or formula (IIh):

FPCPLPYCWLCRALIKRIQAMIPKGGRMLPQLVCRLVLRCS (IIe)     (SEQ ID NO: 13)
   FPIPLPYCWLCRALIKRIQAMIPKGGRMLPQLVCRLVLRCS (IIf)     (SEQ ID NO: 14)
   FPCPLPYCWLCRALIKRIQALIPKGGRLLPQLVCRLVLRCS (IIg)     (SEQ ID NO: 15)
   FPIPLPYCWLCRALIKRIQALIPKGGRLLPQLVCRLVLRCS (IIh),     (SEQ ID NO: 16)

which may be in the form of a disulfide linked molecule wherein the linkage is between the C residues at positions 8 and 40 and/or between the C residues at positions 11 and 34.

5. A reconstituted surfactant according to claim 1, wherein the naturally-derived fraction of unsaturated phospholipids is a L-α-phosphatidylcholine derived from egg yolk.

6. A pharmaceutical formulation, comprising a reconstituted surfactant according to claim 1 in combination with one or more pharmaceutically acceptable carriers.

7. A pharmaceutical formulation according to claim 6, wherein said formulation is in the form of an aqueous suspension.

8. A pharmaceutical formulation according to claim 7, wherein said reconstituted surfactant is present in a concentration of 5 to 100 mg/ml of the aqueous suspension.

9. A kit, comprising:
   (a) a reconstituted surfactant according to claim 1 in powder form in a first unit dosage form;
   (b) a pharmaceutically acceptable carrier in a second unit dosage form; and
   (c) containers containing said first and second dosage forms.

10. A reconstituted surfactant according to claim 1, wherein said polypeptide analogue of formula (II) is represented by formula (IIa):

CWLCRALIKRIQAMIPKGGRMLPQLVCRLVLRCS (IIa)     (SEQ ID NO: 9)

which may be in the form of a disulfide linked molecule wherein the intramolecular disulfide linkage is between the two C residues in positions 1 and 33 and/or between the two C residues in positions 4 and 27.

11. A reconstituted according to claim 1, wherein said polypeptide analogue of formula (II) is represented by formula (IIb):

```
                                      (SEQ ID NO: 10)
CLLCRALIKRIQAMIPKGGRMLPQLVCRLVLRCS            (IIb)
``` which may be in the form of a disulfide linked molecule wherein the intramolecular disulfide linkage is between the two C residues in positions 1 and 33 and/or between the two C residues in positions 4 and 27.

12. A reconstituted surfactant according to claim 1, wherein said polypeptide analogue of formula (II) is represented by formula (IIc):

```
                                      (SEQ ID NO: 11)
CWLCRALIKRIQALIPKGGRLLPQLVCRLVLRCS            (IIc)
``` which may be in the form of a disulfide linked molecule wherein the intramolecular disulfide linkage is between the two C residues in positions 1 and 33 and/or between the two C residues in positions 4 and 27.

13. A reconstituted surfactant according to claim 1, wherein said polypeptide analogue of formula (II) is represented by formula (IId):

```
                                      (SEQ ID NO: 12)
CLLCRALIKRIQALIPKGGRLLPQLVCRLVLRCS,           (IId)
``` which may be in the form of a disulfide linked molecule wherein the intramolecular disulfide linkage is between the two C residues in positions 1 and 33 and/or between the two C residues in positions 4 and 27.

14. reconstituted surfactant according to claim 1, wherein said polypeptide of formula (II) is represented by formula (IIe):

```
                                      (SEQ ID NO: 13)
FPCPLPYCWLCRALIKRIQAMIPKGGRMLPQLVCRLVLRCS     (IIe)
``` which may be in the form of a disulfide linked molecule wherein the linkage is between the C residues at positions 8 and 40 and/or between the C residues at positions 11 and 34.

15. A reconstituted surfactant according to claim 1, wherein said polypeptide of formula (II) is represented by formula (IIf):

```
                                      (SEQ ID NO: 14)
FPIPLPYCWLCRALIKRIQAMIPKGGRMLPQLVCRLVLRCS     (IIf)
``` which may be in the form of a disulfide linked molecule wherein the linkage is between the C residues at positions 8 and 40 and/or between the C residues at positions 11 and 34.

16. A reconstituted surfactant according to claim 1, wherein said polypeptide of formula (II) is represented by formula (IIg):

```
                                      (SEQ ID NO: 15)
FPCPLPYCWLCRALIKRIQALIPKGGRLLPQLVCRLVLRCS     (IIg)
``` which may be in the form of a disulfide linked molecule wherein the linkage is between the C residues at positions 8 and 40 and/or between the C residues at positions 11 and 34.

17. A reconstituted surfactant according to claim 1, wherein said polypeptide of formula (II) is represented by formula (IIh):

```
                                      (SEQ ID NO: 16)
FPIPLPYCWLCRALIKRIQALIPKGGRLLPQLVCRLVLRCS     (IIh)
``` which may be in the form of a disulfide linked molecule wherein the linkage is between the C residues at positions 8 and 4 and/or between the C residues at positions 11 and 34.

18. A method for the treatment or prophylaxis of respiratory distress syndrome in a prematurely born baby or for the treatment or prophylaxis of another disease related to a surfactant-deficiency or dysfunction, comprising administering an effective amount of a reconstituted surfactant according to claim 1 to a subject in need thereof.

19. A method according to claim 18, wherein said another disease is respiratory distress syndrome in an adult, meconium aspiration syndrome and bronchopulmonary dysplasia.

* * * * *

SEQUENCE LISTING

```
<160> NUMBER OF SEQ ID NOS: 21

<210> SEQ ID NO 1
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (31)..(31)
<223> OTHER INFORMATION: Met, Met oxidized on the sulfur atom, Ile,
      Leu, or Nle, and this region may or may not be present
<220> FEATURE:
<221> NAME/KEY: MOD_RES
<222> LOCATION: (32)..(32)
<223> OTHER INFORMATION: This region may or may not be present
<220> FEATURE:
<221> NAME/KEY: MOD_RES
<222> LOCATION: (33)..(33)
<223> OTHER INFORMATION: This region may or may not be present

<400> SEQUENCE: 1

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
            20                  25                  30

Leu

<210> SEQ ID NO 2
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 2

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Met Gly
            20                  25                  30
```

Leu

```
<210> SEQ ID NO 3
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 3
```

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Ile Gly
            20                  25                  30

Leu

```
<210> SEQ ID NO 4
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 4
```

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Leu Gly
            20                  25                  30

Leu

```
<210> SEQ ID NO 5
<211> LENGTH: 33
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (31)..(31)
<223> OTHER INFORMATION: Nle

<400> SEQUENCE: 5
```

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Xaa Gly
            20                  25                  30

Leu

```
<210> SEQ ID NO 6
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 6
```

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu
            20                  25                  30

```
<210> SEQ ID NO 7
```

```
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 7

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Leu
            20                  25                  30

<210> SEQ ID NO 8
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(7)
<223> OTHER INFORMATION: This region may or may not be present
<220> FEATURE:
<221> NAME/KEY: MOD_RES
<222> LOCATION: (3)..(3)
<223> OTHER INFORMATION: Leu, Ile, or Cys
<220> FEATURE:
<221> NAME/KEY: MOD_RES
<222> LOCATION: (9)..(9)
<223> OTHER INFORMATION: Trp, Ile, or Leu
<220> FEATURE:
<221> NAME/KEY: MOD_RES
<222> LOCATION: (21)..(21)
<223> OTHER INFORMATION: Met, Ile, Leu, or Nle
<220> FEATURE:
<221> NAME/KEY: MOD_RES
<222> LOCATION: (28)..(28)
<223> OTHER INFORMATION: Met, Ile, Leu, or Nle
<220> FEATURE:
<221> NAME/KEY: MOD_RES
<222> LOCATION: (39)..(39)
<223> OTHER INFORMATION: Arg or Thr

<400> SEQUENCE: 8

Phe Pro Xaa Pro Leu Pro Tyr Cys Xaa Leu Cys Arg Ala Leu Ile Lys
1               5                   10                  15

Arg Ile Gln Ala Xaa Ile Pro Lys Gly Gly Arg Xaa Leu Pro Gln Leu
            20                  25                  30

Val Cys Arg Leu Val Leu Xaa Cys Ser
        35                  40

<210> SEQ ID NO 9
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 9

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 10
<211> LENGTH: 34
<212> TYPE: PRT
```

<213> ORGANISM: Artificial Sequence
<220> FEATURE:
<223> OTHER INFORMATION: Synthetic Peptide

<400> SEQUENCE: 10

Cys Leu Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 11
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 11

Cys Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser

<210> SEQ ID NO 12
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 12

Cys Leu Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser

<210> SEQ ID NO 13
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 13

Phe Pro Cys Pro Leu Pro Tyr Cys Trp Leu Cys Arg Ala Leu Ile Lys
1               5                   10                  15

Arg Ile Gln Ala Met Ile Pro Lys Gly Gly Arg Met Leu Pro Gln Leu
            20                  25                  30

Val Cys Arg Leu Val Leu Arg Cys Ser
            35                  40

<210> SEQ ID NO 14
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 14

```
Phe Pro Ile Pro Leu Pro Tyr Cys Trp Leu Cys Arg Ala Leu Ile Lys
1               5                   10                  15

Arg Ile Gln Ala Met Ile Pro Lys Gly Gly Arg Met Leu Pro Gln Leu
            20                  25                  30

Val Cys Arg Leu Val Leu Arg Cys Ser
        35                  40
```

```
<210> SEQ ID NO 15
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 15

Phe Pro Cys Pro Leu Pro Tyr Cys Trp Leu Cys Arg Ala Leu Ile Lys
1               5                   10                  15

Arg Ile Gln Ala Leu Ile Pro Lys Gly Gly Arg Leu Leu Pro Gln Leu
            20                  25                  30

Val Cys Arg Leu Val Leu Arg Cys Ser
        35                  40
```

```
<210> SEQ ID NO 16
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 16

Phe Pro Ile Pro Leu Pro Tyr Cys Trp Leu Cys Arg Ala Leu Ile Lys
1               5                   10                  15

Arg Ile Gln Ala Leu Ile Pro Lys Gly Gly Arg Leu Leu Pro Gln Leu
            20                  25                  30

Val Cys Arg Leu Val Leu Arg Cys Ser
        35                  40
```

```
<210> SEQ ID NO 17
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Cys, Ala, Gly, Leu, or Ile
<220> FEATURE:
<221> NAME/KEY: MOD_RES
<222> LOCATION: (2)..(2)
<223> OTHER INFORMATION: Trp, Leu, Nle, or Ile
<220> FEATURE:
<221> NAME/KEY: MOD_RES
<222> LOCATION: (4)..(4)
<223> OTHER INFORMATION: Cys, Leu, or Ile
<220> FEATURE:
<221> NAME/KEY: MOD_RES
<222> LOCATION: (21)..(21)
<223> OTHER INFORMATION: Cys, Leu, or Ile
<220> FEATURE:
<221> NAME/KEY: MOD_RES
<222> LOCATION: (27)..(27)
<223> OTHER INFORMATION: Cys, Ala, Gly, Leu, or Ile
<220> FEATURE:
<221> NAME/KEY: MOD_RES
<222> LOCATION: (28)..(28)
<223> OTHER INFORMATION: Ser, Gly, or Ala, and this region may or may
      not be present
```

```
<400> SEQUENCE: 17

Xaa Xaa Leu Xaa Arg Ala Leu Ile Lys Arg Phe Asn Arg Tyr Leu Thr
1               5                   10                  15

Pro Gln Leu Val Xaa Arg Leu Val Leu Arg Xaa Xaa
            20                  25

<210> SEQ ID NO 18
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 18

Cys Leu Leu Cys Arg Ala Leu Ile Lys Arg Phe Asn Arg Tyr Leu Thr
1               5                   10                  15

Pro Gln Leu Val Cys Arg Leu Val Leu Arg Cys
            20                  25

<210> SEQ ID NO 19
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 19

Cys Trp Leu Cys Arg Ala Leu Ile Lys Arg Phe Asn Arg Tyr Leu Thr
1               5                   10                  15

Pro Gln Leu Val Cys Arg Leu Val Leu Arg Cys
            20                  25

<210> SEQ ID NO 20
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 20

Ala Leu Leu Cys Arg Ala Leu Ile Lys Arg Phe Asn Arg Tyr Leu Thr
1               5                   10                  15

Pro Gln Leu Val Cys Arg Leu Val Leu Arg Ala Ala
            20                  25

<210> SEQ ID NO 21
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 21

Gly Leu Leu Cys Arg Ala Leu Ile Lys Arg Phe Asn Arg Tyr Leu Thr
1               5                   10                  15

Pro Gln Leu Val Cys Arg Leu Val Leu Arg Gly Gly
            20                  25
```